United States Patent
Novak

(10) Patent No.: US 11,224,700 B2
(45) Date of Patent: *Jan. 18, 2022

(54) DELIVERY TOOL OF A VISCOELASTIC SYRINGE ASSEMBLY

(71) Applicant: Anthony Novak, Lake Elmo, MN (US)

(72) Inventor: Anthony Novak, Lake Elmo, MN (US)

(73) Assignee: Anthony Novak, Lake Elmo, MN (US)

( * ) Notice: Subject to any disclaimer, the term of this patent is extended or adjusted under 35 U.S.C. 154(b) by 347 days.

This patent is subject to a terminal disclaimer.

(21) Appl. No.: 16/440,318

(22) Filed: Jun. 13, 2019

(65) Prior Publication Data

US 2019/0290861 A1    Sep. 26, 2019

Related U.S. Application Data

(63) Continuation of application No. 15/799,058, filed on Oct. 31, 2017, now Pat. No. 10,350,370, which is a continuation of application No. 14/508,150, filed on Oct. 7, 2014, now Pat. No. 9,867,952.

(51) Int. Cl.
| | |
|---|---|
| *A61M 5/34* | (2006.01) |
| *A61F 9/00* | (2006.01) |
| *A61M 5/32* | (2006.01) |
| *A61F 9/007* | (2006.01) |

(52) U.S. Cl.
CPC ............ *A61M 5/343* (2013.01); *A61F 9/0008* (2013.01); *A61F 9/00736* (2013.01); *A61M 5/329* (2013.01); *A61M 5/3286* (2013.01); *A61M 5/3293* (2013.01); *A61M 2005/341* (2013.01)

(58) Field of Classification Search
CPC .......... A61M 5/32; A61M 5/34; A61M 5/343; A61M 5/3286; A61M 5/329; A61M 5/3293; A61M 2005/341; A61F 9/00; A61F 9/0008

See application file for complete search history.

(56) References Cited

U.S. PATENT DOCUMENTS

| | | | |
|---|---|---|---|
| 3,661,144 A | 5/1972 | Jensen et al. | |
| 3,955,579 A | 5/1976 | Bridgman | |
| 5,013,295 A | 5/1991 | Dubroff | |
| 5,792,099 A | 8/1998 | DeCamp et al. | |
| 6,413,245 B1 * | 7/2002 | Yaacobi | A61F 9/0017 604/264 |
| 6,802,829 B2 | 10/2004 | Buono | |
| 7,001,362 B2 | 2/2006 | Vincent | |
| 2011/0004057 A1 | 1/2011 | Goldfarb et al. | |
| 2011/0009829 A1 | 1/2011 | Kosinski et al. | |

OTHER PUBLICATIONS

International Search Report and Written Opinion for PCT/US15/54513, dated Nov. 19, 2015 (10 pgs).
The prosecution history for U.S. Appl. No. 14/508,150.
The prosecution history for U.S. Appl. No. 15/799,058.

* cited by examiner

*Primary Examiner* — Tiffany Legette
(74) *Attorney, Agent, or Firm* — Dicke, Billig & Czaja, PLLC

(57) ABSTRACT

A delivery tool connectable with a syringe can be used to deliver a viscoelastic solution. The tool includes a first segment, a second segment and an inner lumen defined by the first and second segments. A distal portion extends from the second segment in a curved manner.

19 Claims, 3 Drawing Sheets

DELIVERY TOOL OF A VISCOELASTIC SYRINGE ASSEMBLY

CROSS-REFERENCE TO RELATED APPLICATIONS

This application is a continuation of U.S. application Ser. No. 15/799,058, filed Oct. 31, 2017, now allowed, and entitled "Delivery Tool of a Viscoelastic Syringe Assembly" which is a continuation of U.S. application Ser. No. 14/508,150, filed Oct. 7, 2014, now U.S. Pat. No. 9,867,952, issued Jan. 16, 2018, and entitled "Delivery Tool of a Viscoelastic Syringe Assembly"; the entire teachings of which are incorporated herein by reference.

BACKGROUND

Cataract surgeries generally involve one or more tools to provide an incision in the cornea and ultimately remove a cataract. After the incision, in current surgical techniques, a viscoelastic solution is delivered into an anterior chamber defined by the cornea such that the cornea is protected during removal of the cataract and, if utilized, placement of an intraocular lens implant. In one current surgical technique, called phacoemulsification, an ultrasonic probe is inserted through the incision. The probe then vibrates, causing emulsification of the cataract. The cataract is then aspirated from the eye along with the injected viscoelastic solution. Due to care and precision required to perform cataract surgeries, approaches to improving surgical techniques for removal of cataracts is desired.

SUMMARY

A delivery tool connectable to a syringe can be used to deliver a viscoelastic solution. The tool includes a first segment, a second segment and an inner lumen defined by the first and second segments. A distal portion extends from the second segment in a curved manner.

DETAILED DESCRIPTION

In the following detailed description, reference is made to the accompanying drawings which form a part hereof, and in which is shown by way of illustration specific examples in which the disclosure may be practiced. It is to be understood that other examples may be utilized and structural or logical changes may be made without departing from the scope of the present disclosure. The following detailed description, therefore, is not to be taken in a limiting sense, and the scope of the present disclosure is defined by the appended claims. It is to be understood that features of the various examples described herein may be combined, in part or whole, with each other, unless specifically noted otherwise.

While the disclosure refers to illustrative embodiments for particular applications, it should be understood that the disclosure is not limited thereto. Modifications can be made to the embodiments described herein without departing from the spirit and scope of the present disclosure. Those skilled in the art with access to this disclosure will recognize additional modifications, applications, and embodiments within the scope of this disclosure and additional fields in which the disclosed examples could be applied. Therefore, the following detailed description is not meant to be limiting. Further, it is understood that the systems and methods described below can be implemented in many different embodiments. The operation and behavior of the systems and methods presented are described with the understanding that modifications and variations of the embodiments are possible given the level of detail presented.

References to "one embodiment," "an embodiment," "in certain embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Figure 1:
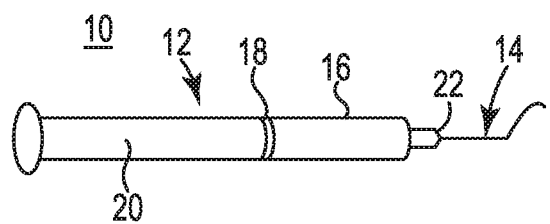
FIG. 1 is a side view of a viscoelastic syringe assembly.

FIG. 1 is a side view of an exemplary syringe assembly 10 that includes a syringe 12 and a delivery tool 14 fluidly coupled with the syringe 12. Syringe 12 includes a cylindrical body 16, a plunger 18 and a rod 20 coupled with the plunger 18. During use, fluid (e.g., a viscoelastic solution) is positioned within the cylindrical body 16. A user can operate the rod 20 to move the plunger 18 relative to the cylindrical body 12 along a longitudinal axis A. To provide fluid to the delivery tool 14, the plunger 18 is actuated toward an orifice 22 that is fluidly coupled with the delivery tool 14. From the orifice 22, the fluid enters the delivery tool 14.

Figure 2:
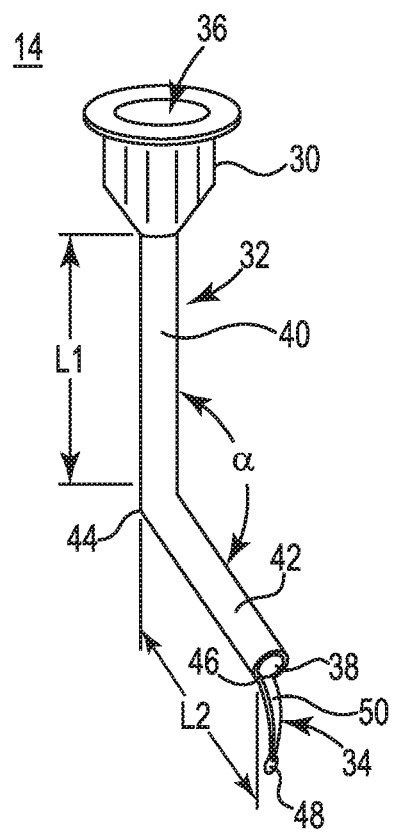
FIG. 2 is an isometric view of a delivery tool connectable to a syringe.

As illustrated in FIG. 2, delivery tool 14 includes a hub 30, a cannula 32 and a distal portion 34 extending from the cannula 32. The hub 30 fluidly communicates with the orifice 22 of the syringe 12 to receive fluid therefrom. In one embodiment, the hub 30 includes a luer lock to establish a leak-free connection between the orifice 22 and the cannula 32. Other types of connections can further be utilized. In one embodiment, the cannula 32 and distal portion 34 are integrally formed of a material useful in biomedical applications such as surgical stainless steel. The cannula 32, in one embodiment, defines a diameter of approximately 27 gauge.

As will be discussed in more detail below, the cannula 32 defines an inner lumen 36 that extends from the hub 30 to a distal opening 38. In particular, the lumen extends from the hub 30, along a first, proximal segment 40, a second, distal segment 42 connected with the first segment 40 and to the distal opening 38. The first segment 40 is connected to the second segment 42 with a bend portion 44 such that second segment 42 is offset with respect to the first segment 40. The second segment 42 extends from the bend portion 44 to a connection point 46 with the distal portion 34.

The distal portion 34 extends from the connection point 46 with second segment 42 in a curved manner to a distal tip 48. A beveled surface 50 extends along one side of the distal portion 34. The distal portion 34 can be formed with a generally circular cross section or with other cross section shapes (e.g., rectangular, oval) as desired. In the illustrated embodiment, a width of the distal portion 34 tapers from a width of approximately 2.0 to 1.0 mm at connection point 46 to a width of approximately 1 to 0.25 mm at distal tip 48. Distal tip 48, in one embodiment, includes a blunt, bulbous tip having a diameter of approximately 0.25 to 2.0 mm. The beveled surface 50 can be formed of a flat (or substantially flat) surface. In an alternative embodiment, the beveled surface 50 can be formed of a curved surface.

Geometric relationship of the first segment 40, second segment 42 and distal portion 34 is discussed below with respect to FIG. 3A. The first segment 40 extends longitudinally from the hub 30 along axis A to bend portion 44. Axis A can be referred to as a central axis of first segment 40. In one embodiment, the first segment 40 defines a length L1 from hub 30 to bend portion 44 of approximately 1.0 centimeters to 3.0 cm. In one particular embodiment, the length L1 of first segment 40 is approximately 2.0 cm.

The second segment 42 extends from the bend portion 44 along a longitudinal axis B to connection point 46. Axis B can be referred to as a central axis of second segment 42. Axis B is positioned at an angle α relative to axis A of first segment 40. In one embodiment, the angle α is approximately in a range from 20 degrees to 90 degrees. In one particular embodiment, the angle α is approximately 45 degrees. The second segment 42 as measured from bend portion 44 to connection point 46, in one embodiment, has a length L2 of approximately 0.5 cm to 1.5 cm. In one particular embodiment, length L2 of second segment 38 is approximately 1.0 cm.

The distal portion 34 extends from the connection point 46 to the distal tip 48 in a curved manner as defined by a curve 52. Curve 52 can be defined as a central axis of the distal portion 34. At least a part of the curve 52 deviates from the axis B and, in one embodiment, an entirety of the curve 52 deviates from axis B. As shown in the illustrated embodiment, the distal portion 34 is positioned below the opening 38 such that distal portion 34 does not have any part that touches axis B. In a further embodiment, at least the distal tip 48 deviates from axis B.

Relative to curve 52, beveled surface 50 is positioned to one side of the distal portion 34. As illustrated in FIG. 3B, when distal portion 34 is viewed in cross section perpendicular to the curve 52, an arc 54 defined by an outer surface of the distal tip 34 extending to either side of beveled surface 50 can be approximately 50 to 320 degrees.

In one embodiment, curve 52 of the distal portion 34 can be defined relative to a Cartesian coordinate system wherein axis B serves as a first axis and an axis C serves as a second axis, perpendicular to axis B. In particular, the curve 52 is a plane curve that extends within a plane BC defined by axes B and C. An origin of the coordinate system is located at the connection point 46. Relative to axis C, distal tip 48 extends from connection point 46 a distance X of approximately 0.3 to 3.5 mm. In one particular embodiment, distance X is approximately 1.5 mm. Additionally, relative to axis B, the distal tip 48 extends from connection point 46 a distance Y (e.g., away from first segment 40) from axis B of approximately 0.5 to 1.5 mm. In one particular embodiment, the distance Y is approximately 1.0 mm from the axis. Moreover, since curve 52 lies in plane BC, a distance Z from plane BC to a distal tip 48 is zero.

A line D connecting the connection point 46 and distal tip 48 defines an angle 3 with respect to axis B that is approximately in a range from 20 to 40 degrees from the axis of the second segment 42. In one particular embodiment, the angle 3 is approximately 30 degrees. A height H of the curve 52 (as defined from line D to a maximum distance from line D) is in a range of 0.1 to 4.5 mm and a width W of the curve 52 along line D is in a range of 0.5 to 2.0 mm. The curve 52 has a radius of curvature of approximately 4.0 to 10 mm.

Figure 3A:
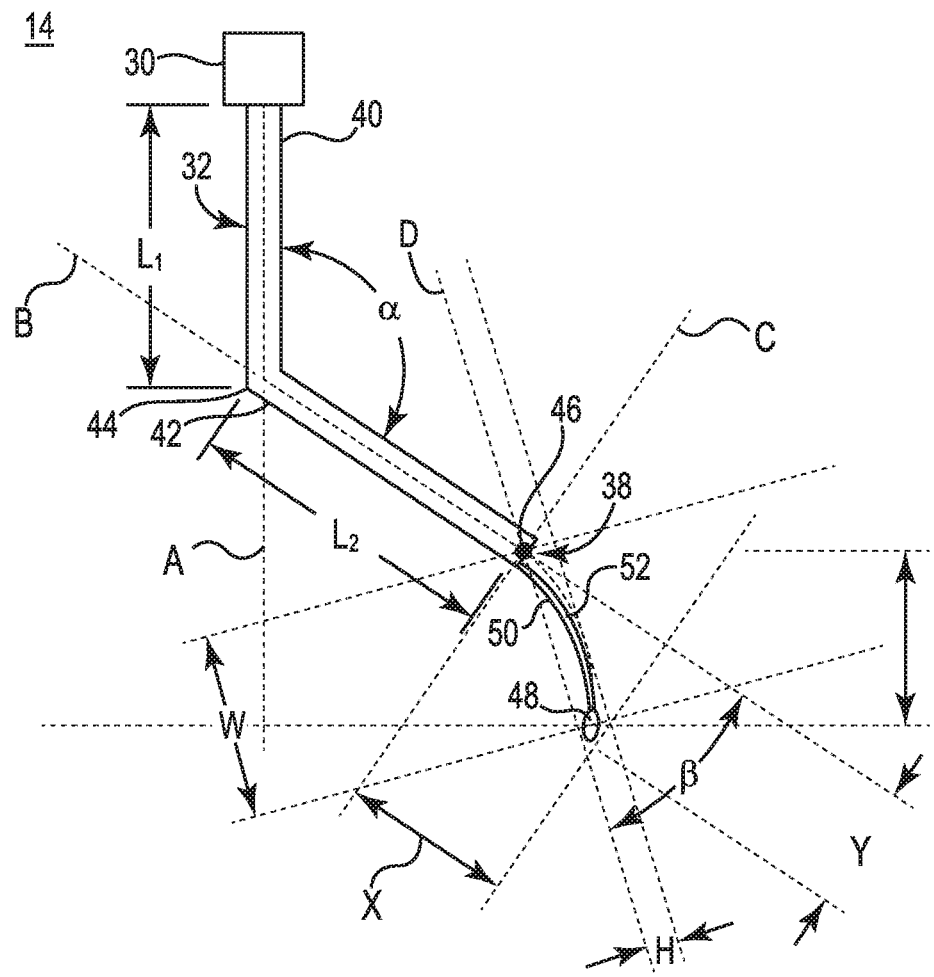
FIG. 3A is a side view of the delivery tool of FIG. 2.
Figure 3B:
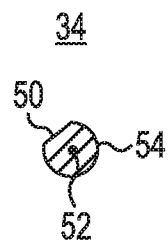
FIG. 3B is a cross sectional view of a portion of the delivery tool of FIG. 2.

In FIG. 3A discussed above, curve 52 is a plane curve defined in two dimensions that lies in a plane defined by axes A, B and C. As such, the embodiment of FIG. 3A can generally be referred to as a straight configuration, wherein the geometric arrangement among central axis of first segment 40, second segment 42 and distal portion 34 can generally be described in two dimensions. In further embodiments, the distal portion 34 can extend from second segment 42 in a curved manner away from a plane defined by axes B and C. For example, the delivery tool 14 can further include a right-handed curvature or a left-handed curvature (as viewed by an operator holding the assembly 10 during use), illustrated in FIGS. 4 and 5, respectively. In such embodiments, the curve of the distal portion 34 can be a space curve defined in three dimensions.

Figure 4:
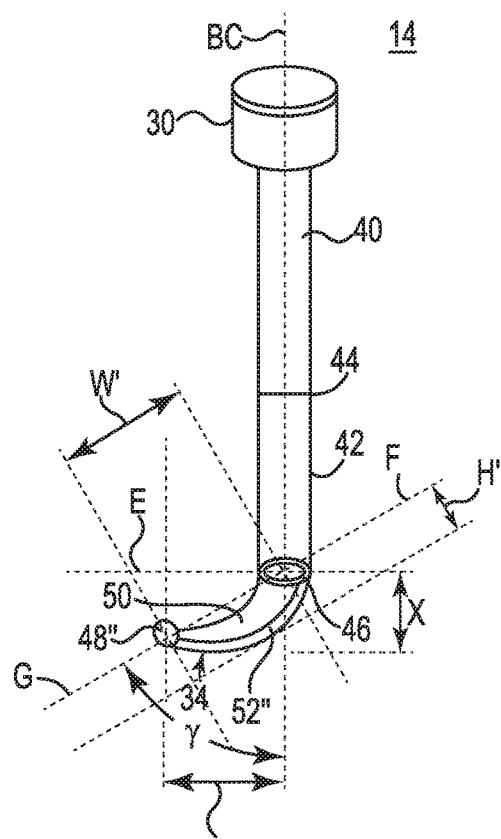
FIG. 4 is a front view of an alternative delivery tool connectable to a syringe.

In FIG. 4 illustrating the right-handed curvature, a distal portion 34' defines a curve 52' extending from connection point 46 to a distal tip 48' in a direction away from plane BC. The curve 52' can extend within plane BC in various ways, for example being coplanar with plane BC or extending in a similar manner to that discussed above with respect to curve 52. While curve 52' will be discussed below relative to a plane including plane BC and extending along an axis E perpendicular to plane BC and including connection point 46, it will be appreciated that curve 52' is not limited to only being positioned with respect to axes B and E, but also with respect to axis C. Stated another way, distal tip 48' can be positioned in a direction along axis C in any desired position (including along axis B).

With the above understanding in mind, curve 52' of the distal portion 34 can be defined relative to a Cartesian coordinate system wherein axis B serves as a first axis and axis E serves as a second axis, perpendicular to axis B. In particular, the curve 52' extends within a plane BE defined by axes B and E. An origin of the coordinate system is located at the connection point 46. Relative to axis C along axis B, distal tip 48' extends from connection point 46 a distance X' of approximately 0.1 to 2.0 mm. In one particular embodiment, distance X' is approximately 1.0 mm. Relative to axis B along axis C, for example as discussed above with respect to curve 50, the distal tip 48' extends from connection point 46 a distance Y' from axis B of approximately 0.5 to 1.5 mm. In one particular embodiment, the distance Y' is approximately 1.0 mm from the axis. Relative to axis E along axis B, the distal tip 34 extends a distance Z' of approximately 0.1 to 2.5 mm. In one embodiment, distance Z' is approximately 1.0 mm.

A line F connecting the connection point 46 and distal tip 48' defines an angle γ with respect to axis B that is approximately in a range from 20 to 40 degrees from the axis of the second segment 42. In one particular embodiment, the angle γ is approximately 25 degrees. A height H' of the curve 52' (as defined from line F to a maximum distance of curve 52' from line F) is in a range of 0.1 to 1.0 mm and a width W' of the curve 52' along line F is in a range of 0.1 to 1.0 mm. The curve 52' has a radius of curvature of approximately 4.0 to 10.0 mm.

Figure 5:
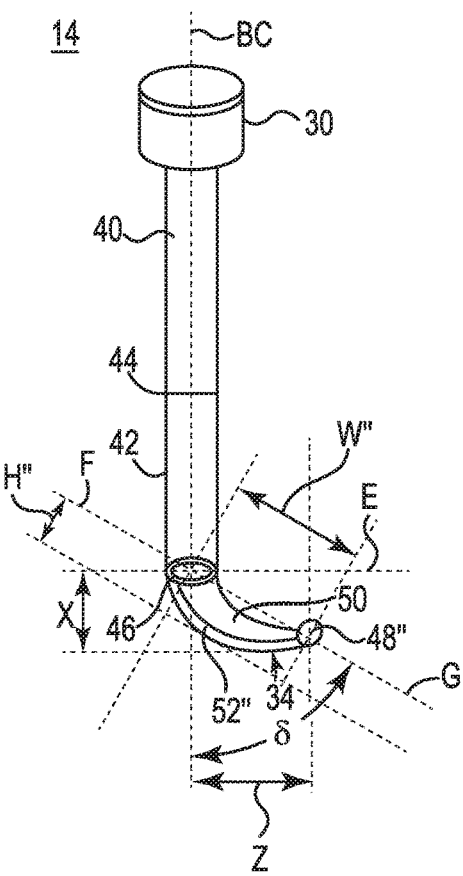
FIG. 5 is a front view of an alternative delivery tool connectable to a syringe.

In FIG. 5 illustrating the left-handed curvature, a distal portion 34" defines a curve 52" extending from connection point 46 to a distal tip 48" in a direction away from plane BC in an opposite direction from distal portion 34'. The curve 52" can extend within plane BC in various ways, for example being coplanar with plane BC or extending in a similar manner to that discussed above with respect to curve 52. While curve 52" will be discussed below relative to a plane including plane BC and extending along an axis E perpendicular to plane BC and including connection point 46, it will be appreciated that curve 52" is not limited to only being positioned with respect to axes B and E, but also with respect to axis C. Stated another way, distal tip 48" can be positioned along axis C in any desired position (including along axis B).

With the above understanding in mind, curve 52" of the distal portion 34" can be defined relative to a Cartesian coordinate system wherein axis B serves as a first axis and axis E serves as a second axis, perpendicular to axis B. In particular, the curve 52" extends within a plane BE defined by axes B and E. An origin of the coordinate system is located at the connection point 46. Relative to axis C along axis B, distal tip 48" extends from connection point 46 a distance X" of approximately 0.1 to 2.5 mm. In one particular embodiment, distance X" is approximately 1.0 mm. Additionally, relative to axis B along axis C, the distal tip 48" extends from connection point 46 a distance Y" from axis B of approximately 0.5 to 1.5 mm. In one particular embodiment, the distance Y" is approximately 1.0 mm from the axis. Relative to axis E along axis B, the distal tip 34 extends a distance Z" of approximately 0.1 to 2.5 mm. In one embodiment, Z" is approximately 1.0 mm.

A line G connecting the connection point 46 and distal tip 48" defines an angle δ with respect to axis B that is approximately in a range from 20 to 40 degrees from the axis of the second segment 42. In one particular embodiment, the angle δ is approximately 25 degrees. A height H" of the curve 52" (as defined from line G to a maximum distance of curve 52" from line G) is in a range of 0.1 to 1.5 mm and a width W" of the curve 52" along line G is in a range of 0.1 to 1.5 mm. The curve 52" has a radius of curvature of approximately 4.0 to 10.5 mm.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A delivery tool connectable to a syringe, the delivery tool comprising:
   a cannula having an inner lumen that terminates at a distal opening; and
   a tip portion including a curve defined as a central axis of the tip portion, the tip portion including a surface extending from and fixed to a portion of the cannula that forms the distal opening, wherein opposite the cannula, the tip portion has a distal tip having a substantially bulbous tip fixed to the surface that originates at a distal end of the surface such that the substantially bulbous tip is separated from the distal opening by the surface, wherein, the surface includes a bevel and, relative to the curve, the bevel is positioned to one side of the tip portion.

2. The delivery tool of claim 1, wherein the substantially bulbous tip has a width that is less than an outer diameter of the cannula.

3. The delivery tool of claim 1, wherein the surface tapers from the distal opening to the distal tip.

4. The delivery tool of claim 1, wherein bevel is a planar surface.

5. The delivery tool of claim 1, wherein the bevel is a curved surface.

6. The delivery tool of claim 1, wherein the distal tip is rigid and the substantially bulbous tip has an external surface; wherein the delivery tool is arranged and configured to direct fluid from the cannula, to the surface and then over the external surface of the substantially bulbous tip.

7. The delivery tool of claim 1, wherein the substantially bulbous tip is ovoid.

8. The delivery tool of claim 1, wherein an arc defined by an outer surface of the tip portion extending to either side of the bevel is in a range of 50 to 320 degrees.

9. The delivery tool of claim 1, wherein the bevel is a flat surface.

10. The delivery tool of claim 1, wherein the cannula includes a first segment and a second segment.

11. The delivery tool of claim 10, wherein the second segment extends outwardly from a first central axis of the first segment at an angle.

12. A syringe assembly, comprising:
    a delivery tool including:
    a cannula having an inner lumen that terminates at a distal opening; and
    a tip portion including a curve defined as a central axis of tip portion, the tip portion including a surface extending from and fixed to a portion of the cannula that forms the distal opening, wherein opposite the cannula, the tip portion has a distal tip having a substantially bulbous tip fixed to the surface that originates at a distal end of the surface such that the substantially bulbous tip is separated from the distal opening by the surface, wherein, the surface includes a bevel and, relative to the curve, the bevel is positioned to one side of the tip portion; and
    a syringe connected to the delivery tool.

13. The syringe assembly of claim 12, wherein a central axis of the syringe is aligned with a central axis of the cannula, the syringe including a plunger and rod such that, upon actuation of the rod, fluid is delivered to the inner lumen of the delivery tool.

14. The syringe assembly of claim 12, wherein the substantially bulbous tip has a width that is less than an outer diameter of the cannula.

15. The syringe assembly of claim 12, wherein the surface tapers from the distal opening to the distal tip.

16. The syringe assembly of claim 12, wherein bevel is a planar surface.

17. The syringe assembly of claim 12, wherein the bevel is a curved surface.

18. The syringe assembly of claim 12, wherein an arc defined by an outer surface of the tip portion extending to either side of the bevel is in the range of 50 to 320 degrees.

19. The syringe assembly of claim 12, wherein the bevel is a flat surface.

* * * * *